United States Patent [19]
Trevithick

[11] Patent Number: 5,193,685
[45] Date of Patent: Mar. 16, 1993

[54] GEMSTONE SORTING APPARATUS AND METHODS

[76] Inventor: William J. Trevithick, 1620 Crespo Dr., LA Jolla, Calif. 92037

[21] Appl. No.: 718,014

[22] Filed: Jun. 20, 1991

[51] Int. Cl.$^5$ ............................................. B07C 5/02
[52] U.S. Cl. .................................. 209/3.1; 209/552; 209/589; 209/698; 209/932; 324/71.4; 414/224
[58] Field of Search ................ 209/3.1, 3.3, 551, 552, 209/576, 589, 606, 698, 920, 925; 414/222, 224; 250/308; 198/372, 493; 324/71.4; 376/159

[56] References Cited

U.S. PATENT DOCUMENTS

| | | | |
|---|---|---|---|
| 3,052,353 | 9/1962 | Pritchett | 376/159 X |
| 3,313,410 | 4/1967 | Gardner | 209/920 X |
| 3,743,093 | 7/1973 | Klancnik | 209/920 X |
| 4,214,663 | 7/1980 | Schopp et al. | 198/372 X |
| 4,483,651 | 11/1984 | Nakane et al. | 198/341 X |
| 4,528,680 | 7/1985 | Archambeault | 209/551 X |
| 4,717,026 | 1/1988 | Fischer et al. | 209/551 X |
| 4,749,869 | 6/1988 | Fournier | 250/492.1 |
| 4,830,193 | 5/1989 | Clayton et al. | 209/3.1 |

FOREIGN PATENT DOCUMENTS

| | | | |
|---|---|---|---|
| 2741788 | 1/1979 | Fed. Rep. of Germany | 198/372 |
| 2188722 | 10/1987 | United Kingdom | 209/576 |

OTHER PUBLICATIONS

Kaplan, *IEEE Spectrum*, 27:42–43 (Feb. 1990), "Industrial Electronics".
Whittaker, et al.; *IEEE Spectrum*, 27:64–67 (Dec. 1990), "Japan Robotics Aim for Unmanned Space Exploration".

*Primary Examiner*—Andres Kashnikow
*Assistant Examiner*—Joseph A. Kaufman

[57] ABSTRACT

An automated gemstone sorting apparatus and method that handles, tests, and sorts a batch of irradiated topaz, or similar gemstones, in an efficient manner in accordance with residual radiation levels. The sorting apparatus and methods of the invention include a system of three parallel conveyors, i.e., input, accept and reject conveyors, as well as a vibrator bowl for automatically loading the gemstones in an orderly fashion onto the input conveyor. A multiplicity of isolated testing chambers is located to the side of the conveyor systems, each having a radiation detector and appropriate radiation measuring apparatus. Each of the isolated testing chambers has a single robot station associated therewith for manipulating the gemstones into and out of its respective testing chamber. Each robot station includes a pneumatic "puffer", responsive to a sensing device for directing a puff of air at a specified point on the input conveyor belt when a gemstone is sensed at the specified point. The puff of air moves the gemstone off the input conveyor and into a receptacle on a probe arm. The probe arm delivers the gemstone to the isolated testing chamber and radiation detector and, after testing, delivers the gemstone to either the accept conveyor or the reject conveyor. A computer monitors and controls the sorting apparatus, and provides various data associated with the testing and sorting of the gemstone batch.

8 Claims, 7 Drawing Sheets

GEMSTONE SORTING APPARATUS AND METHODS

BACKGROUND OF THE INVENTION

The present invention relates to apparatus and methods for sorting gemstones according to predetermined characteristics and, in particular, to apparatus and methods for testing and sorting, i.e., classifying, previously irradiated topaz gemstones according to their residual radiation levels.

The technique of irradiating white topaz in order to change its color to blue is described, e.g, in U.S. Pat. No. 4,749,869, issued to Fournier, which patent is incorporated herein by reference. Once topaz is irradiated it continues to be radioactive for some months afterwards. Before the irradiated topaz can be used by jewelers and others, i.e., before it can be placed in the public domain, its residual gamma radiation must be less than certain prescribed limits that are set by the Nuclear Regulatory Commission (NRC) or other regulatory agencies. These limits are very low, almost at the levels of common background radiation, making measurements of the residual radiation very difficult.

Hence, immediately after being irradiated (when the residual gamma radiation is the highest), the blue topaz must be stored in shielded containers until such time as the residual gamma radiation of each stone is within the prescribed limits. Because the residual gamma radiation varies as a function of stone size, shape and weight, the white topaz is usually presorted into batches of prescribed sizes, shapes, and weights (e.g., 3 mm, 4 mm, 5 mm, 6×4 mm, etc.) commonly used by jewelers and others in the industry prior to being irradiated, and remains sorted into such batches during and after irradiation.

After being held in shielded storage for an estimated time period (smaller-sized gemstones tend to retain their residual radiation longer than larger-sized gemstones), which may be four to twelve months, a given batch of blue topaz is retrieved from storage, and each gemstone within the batch is checked to see if its residual radiation is within the prescribed limits. If so, the gemstone is placed in a batch suitable for distribution. If not, the gemstone is placed in a batch that is returned to storage.

Because the prescribed limits on residual radiation are extremely low, it is necessary (when checking the radiation levels of each gemstone) to place the gemstone in a shielded container, e.g., a lead enclosure, where the residual radiation can be accurately measured in the absence of common background radiation. As indicated above, if the residual radiation is below the prescribed limits set by the NRC or other regulatory agency, the topaz is classified as acceptable. If the residual radiation is greater than the prescribed limits, the topaz is classified as not acceptable, and it is placed back in a shielded container and stored for an additional length of time, after which time its residual radiation is again measured.

Unfortunately, heretofore this process of checking the residual radiation of each blue topaz gemstone is extremely labor and time intensive. Not only must each stone or small parcel of stones be handled individually, in order to place the stone in a suitable shielded chamber where a radiation measurement may be made, but the radiation measurement itself takes several seconds, typically up to 20-30 seconds, to complete. Further, if statistical data associated with the radiation measurement is to be made, the logging and processing of such data may further slow down the measurement process. Hence, the rate at which the stones can be classified is severely limited. What is needed, therefore, is an apparatus and method that carries out this classifying process automatically, with minimal supervision, and at a high rate of throughput.

SUMMARY OF THE INVENTION

The present invention advantageously addresses the above and other needs by providing an automated gemstone sorting apparatus and method that handles, tests, and sorts a batch of irradiated topaz, or similar gemstones, in a highly efficient manner. Further, in accordance with one aspect of the invention, various data associated with the testing and sorting of the gemstone batch may be selectively and readily processed and/or reported.

The present invention provides apparatus and methods for automatically sorting previously irradiated topaz or similar gemstones according to residual radiation levels. To accomplish this sorting function, the apparatus and methods of the invention include: (1) transport means for moving the gemstones from an initial location to classified final locations; (2) testing means for determining if the residual radiation of the topaz gemstones is within prescribed limits; and (3) manipulating means for removing the gemstones from the transport means, placing them in the testing means, and then returning them to the transport means for further transport to the appropriate classified final location as a function of whether the residual radiation of the gemstones is within the prescribed limits.

In the preferred embodiment of the invention, the transport means includes a system of three parallel conveyors, i.e., input, accept and reject conveyors, as well as a means for automatically loading the gemstones in an orderly fashion onto the input conveyor. The testing means includes a multiplicity of isolated testing chambers located on one side of the conveyor systems, each having a radiation detector contained therein, and each having appropriate radiation measuring apparatus associated therewith. The manipulating means includes a robot table located on the other side of the conveyor systems, which robot table includes a multiplicity of gemstone handling stations. Each of the isolated testing chambers has a single gemstone handling station associated therewith for manipulating the gemstones into and out of its respective testing chamber.

Each gemstone handling station includes a fluid nozzle, e.g., a pneumatic "puffer", responsive to a sensing device for directing a puff of fluid, e.g., air, at a specified point on the input conveyor belt when a gemstone is sensed at the specified point. The puff of fluid moves the gemstone off the input conveyor and into a receptacle on a probe arm. The probe arm delivers the gemstone to the isolated testing chamber and radiation detector and, after testing, delivers the gemstone to either the accept conveyor or the reject conveyor.

It should be noted that the term "gemstone" as used above and throughout this specification is intended to refer to individual gemstones as well as small parcels of gemstones. The preferred embodiment as described herein is capable of processing both batches of individual gemstones and batches of small parcels of gemstones.

The handling stations are monitored and controlled by a computer through a programmable logic controller. The computer keeps track of which testing stations are currently occupied, and moves (by controlling the operation of the fluid nozzles) the leading gemstone on the input conveyor to the first available testing chamber. If all of the testing chambers are occupied, then the gemstones fall off of the input conveyor into a recycling collection bowl, from which location the stones may be recycled back onto the input conveyor.

The computer also receives input data from the radiation detectors and associated radiation measuring equipment, and determines if the residual radiation of a particular gemstone in a particular testing chamber is acceptable. If so, the computer instructs the programmable logic controller to place that particular gemstone on the accept conveyor. If the residual radiation level is not acceptable, the computer instructs the programmable logic controller to place that particular gemstone on the reject conveyor. The accept/reject conveyors then carry the gemstones placed thereon to respective collection bowls at the end of each conveyor. The gemstones in the accept collection bowl may then be distributed in the public domain. The gemstones in the reject collection bowl are placed in a shielded storage container and stored for an additional length of time, after which time they may be reinserted into the sorting apparatus.

Another embodiment of the invention may also be characterized as an automated classifying system for classifying irradiated gemstones according to residual radiation levels. Such classifying system includes: (1) first transport means for automatically moving each gemstone in a batch of gemstones from an initial location to one of a multiplicity of testing stations; (2) measurement means for automatically measuring the radiation of each gemstone moved to one of the multiplicity of testing stations; (3) second transport means for automatically removing a gemstone from a given testing station after its residual radiation has been measured and moving it to one of a plurality of final locations as a function of its residual radiation; and (4) processing means for monitoring and controlling the first and second transport means and measurement means so as to move a new gemstone into a given testing station almost immediately after the second transport means has removed a gemstone therefrom. Advantageously, such a classifying system is able to sort the gemstones in a very efficient manner, with minimal time elapsing when a given testing station is vacant and not being used.

The throughput time for classifying a batch of gemstones, i.e., the time it takes for all of the gemstones in a given batch to be classified, using the classifying system of the present invention is determined in large part by how long it takes to make the radiation measurement at each testing station. Advantageously, however, this throughput time may be minimized by simply increasing the number of testing stations. A typical classifying system, for example, may require 15-25 seconds (20 seconds on average) to perform a residual radiation measurement for each gemstone. Thus, if eight testing stations are used, the overall throughput rate of gemstones in such a system would be on the order of about one gemstone classified each 2.5 seconds, or about 24 gemstones classified per minute. If ten testing stations are used, the average throughput rate increases to about one gemstone classified each 2.0 seconds, or about 30 gemstones classified per minute. Such rates far exceed any that have heretofore been obtainable using manual sorting and classifying techniques.

The present invention may further be viewed and characterized as a method of automatically sorting a batch of gemstones in accordance with the residual radiation level of each gemstone within the batch. Such method is most easily carried out using a gemstone sorting apparatus or a gemstone classifying system as described herein, although the method may also be carried out using equivalent apparatus or systems The method includes the steps of: (a) moving each gemstone in the batch of gemstones from an initial location to one of a multiplicity of testing stations; (b) measuring the residual radiation of each gemstone that is moved to one of the multiplicity of testing stations; (c) removing a gemstone from a given testing station after its residual radiation has been measured and moving it to one of a plurality of final locations as a function of the residual radiation measured for such gemstone; and (d) monitoring and controlling the movement, testing and removing of the gemstones as set forth in steps (a), (b) and (c) above so as to automatically move a new gemstone into a given testing station almost immediately after a previous gemstone has been removed therefrom. Advantageously, with this method all of the testing stations are continually being loaded with a gemstone, testing a gemstone, or having a gemstone removed therefrom. Hence, the batch of gemstones are automatically sorted in as short of time as possible.

It is a feature of the present invention to provide a gemstone sorting apparatus that automatically sorts and classifies irradiated gemstones according to the residual radiation level of each gemstone.

It is another feature of the invention to provide such a gemstone sorting apparatus that allows the sorting and classifying function for a given gemstone to be carried out simultaneous to the sorting and classifying function associated with a multiplicity of other gemstones, whereby the throughput rate of the apparatus is not limited by the individual handling and processing time associated with a single gemstone or small parcel of gemstones.

It is a further feature of the invention to provide such a gemstone sorting apparatus that allows the gemstones being classified to be loaded into a single input receptacle, and that thereafter automatically delivers the gemstones having an acceptable residual radiation level to a first output receptacle, and delivers the gemstones having an unacceptable residual radiation level to a second output receptacle.

It is an additional feature of the invention to provide an automated gemstone classifying system, using gemstone sorting apparatus of the type described herein, that automatically keeps track of the number of gemstones that are examined in a given batch, including providing a visual and/or written report of such number. It is a related feature of such a sorting system to provide processing means that selectively computes the accept/reject statistics of a given batch of gemstones, or similar processing data, and provides a visual and/or written report of the same.

It is yet another feature of the invention to provide a method of classifying a group of gemstones, e.g., topaz, that has been previously irradiated according to the amount of residual radiation emanating from each gemstone within the group.

BRIEF DESCRIPTION OF THE DRAWINGS

The above and other aspects, features and advantages of the present invention will be more apparent from the following more particular description thereof, presented in conjunction with the following drawings wherein:

FIG. 3D is a schematic end view as in FIGS. 3A-3C showing the gemstone and holding receptacle in the reject position;

It is noted that corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
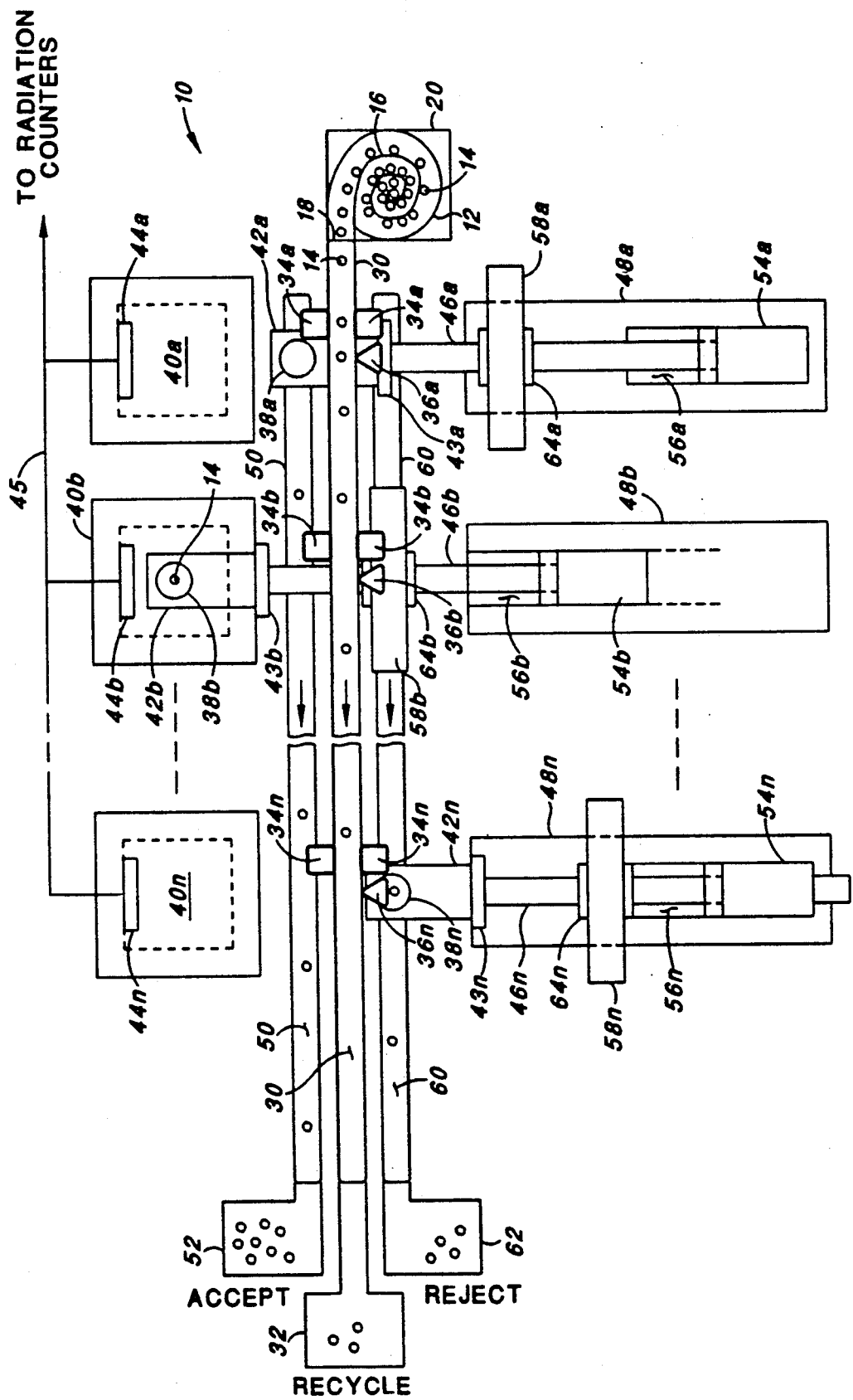
FIG. 1 is a schematic top view of gemstone sorting apparatus constructed according to the teachings of the present invention.

Referring first to FIG. 1, there is shown a schematic top view of gemstone sorting apparatus 10 constructed according to the teachings of the present invention. Basically, the apparatus includes an input conveyor 30 for carrying gemstones past a multiplicity of testing stations 40a, 40b, . . . 40n. When a gemstone passes a vacant testing station, it is removed from the input conveyor 30 and inserted into such vacant test station, as described more fully below. While in the testing chamber, the residual radiation of the gemstone is measured. If the residual radiation of the gemstone is within predefined limits, then that particular gemstone is classified as acceptable, and it is removed from the testing chamber and placed on an accept conveyor 50. The accept conveyor 50 carries the acceptable gemstones to an accept bin 52, where such gemstones may be collected and distributed in normal channels of commerce. If the residual radiation of the gemstone is not within the predefined limits, i.e., if the radiation count measured from the gemstone is too high, then the gemstone is removed from the testing chamber and placed on a reject conveyor 60. The reject conveyor 60 carries the rejected gemstones to a reject bin 62. The gemstones in the reject bin 62 are collected and placed in an appropriate shielded container, and held for a period of time (e.g., one, two or three weeks), after which time they may be re-tested by the apparatus 10. Any gemstones that are not able to be tested because the testing stations 40a, 40b, . . . 40n were not vacant as such gemstones pass by on the input conveyor 30 are collected in a recycle bin 32. The gemstones in the recycle bin 32 may be recycled back to the front of the input conveyor 30 for another pass through the sorting apparatus 10.

As seen in FIG. 1, the input conveyor 30, the accept conveyor 50, and the reject conveyor 60 form a conveyor network of three parallel conveyors. The input conveyor is positioned above the accept and reject conveyors. These conveyors may all be conventional conveyors driven by appropriate electric motors. As will be evident from FIGS. 3A-3D, described below, in a preferred embodiment the reject conveyor 60 is positioned directly beneath the input conveyor 30. However, for purposes of clarity of explanation, the reject conveyor 60 is shown in FIG. 1 as being to the side and beneath the input conveyor 30.

Still referring to FIG. 1, a feeder bowl 12 is positioned at the front end of the input conveyor 30. A batch of gemstones to be sorted is placed in this feeder bowl. The gemstones of the batch being sorted are depicted in the schematic diagram of FIG. 1 as small irregular shapes 14. The feeder bowl 12 includes a spiralling path 16 around its inside edge that carries the gemstones 14 from the bottom of the feeder bowl up to an exit port 18 of the bowl when the bowl is vibrated. The front end of the input conveyor 30 is positioned to receive all of the gemstones 14 that exit from the port 18.

A suitable vibration generator (or vibrator) 20 is mounted beneath the feeder bowl 12 in order to provide the desired vibration. By the time the gemstones reach the exit port 18, they are lined up in single file and spaced substantially evenly. Advantageously, the rate at which the gemstones 14 are carried up the spiralling path 16, as well as the spacing between the gemstones, is controlled by the frequency of the vibrator 20. Thus, by controlling the frequency of the vibrator 20, the gemstones are effectively positioned on the input conveyor 30 in single file, with a substantially uniform spacing therebetween.

The input conveyor 30 carries the gemstones in single file past the testing stations 40a 40b, . . . 40n. As a given gemstone approaches a particular testing station, optical sensors 34a, 34b, . . . 34n sense its presence on the conveyor 30. If the particular testing station that is being approached by the sensed gemstone is vacant, then a pneumatic puffer 36a, 36b, . . . 36n is activated to blow the gemstone off of the input conveyor 30 into a gemstone holding receptacle 38a, 38b, . . . 38n. It is noted that the activation of the pneumatic puffer 36a, 36b, . . . 36n is delayed slightly after first sensing the gemstone in order to give the gemstone adequate time to move directly in front of the respective pneumatic puffer.

Each of the holding receptacles 38a, 38b, . . . 38n is a cavity or cup formed near the end of respective plungers 42a, 42b, . . . 42n. The receptacles 38a, 38b, 38n are sized so as to readily hold one gemstone. Each of the plungers 42a, 42b, . . . 42n, in turn, is supported by respective probe arms 46a, 46b, . . . 46n. These probe arms are controlled, as explained below, to selectively position the respective holding receptacles in one of a plurality of linear positions. In a preferred embodiment there are three such positions of the holding receptacle: (1) adjacent the input conveyor 30 so as to receive a gemstone removed therefrom by the pneumatic puffer (this position is also immediately above the accept conveyor 50); (2) inside of a testing chamber so as to allow the radiation level of the gemstone to be measured; and (3) immediately above the reject conveyor 60.

As schematically depicted in FIG. 1, the holding receptacle 38a is vacant, and is positioned in its first linear position, i.e., so as to receive a gemstone that is blown or "puffed" off of the input conveyor 30. In contrast, the holding receptacle 38b has a gemstone 14 therein and is positioned so that the gemstone is inside of the testing chamber 40b. The holding receptacle 38n, in still further contrast, is shown positioned above the reject conveyor 60.

The residual radiation of a given gemstone is measured when such gemstone is inserted into its respective testing station. Advantageously, the testing stations 40a, 40b, ... 40n are shielded with an appropriate material, such as lead, that prevents most background gamma radiation from entering therein. Thus, the residual gamma radiation of the gemstone is measured in a controlled environment of greatly reduced background gamma radiation (about one-fourth actual background), providing an accurate measure of the residual gamma radiation level associated with that particular gemstone under test. A suitable detector 44a, 44b, ... 44n is placed inside of each testing chamber 40a, 40b, ... 40n, respectively, in order to detect any gamma rays that are emitted from the gemstone in the testing chamber. Such detectors 44a, 44b, ... 44n may be NaI crystals configured in a manner known in the art. In a preferred embodiment, such detectors are 4" by 4" hole-through NaI detectors available from Rexon, of Macedonia, Ohio.

The NaI detectors 44a, 44b, ... 44n emit an electrical pulse upon detection of a gamma ray. These electrical pulses are routed through cables 45 to radiation counting equipment, not shown in FIG. 1. The level of residual radiation is measured by simply counting the number of pulses generated by the respective radiation detector during a prescribed time period or "window". For purposes of measuring the residual radiation of previously irradiated topaz, such measurement time window usually ranges from about 15 to 25 seconds, depending upon the size of the particular topaz stones. A high radiation "count" (i.e., the occurrence of a large number of pulses within the measurement time window) signals a high level of residual radiation. A low radiation count signals a low level of residual radiation.

Because the prescribed radiation level for irradiated gemstones is typically very low (i.e. not different from common background radiation), it is necessary to remove as much background radiation as possible while the measurement is being made. Therefore, as indicated above, the testing stations 40a, 40b, ... 40n are well shielded with an appropriate layer of radiation-absorbing material, such as lead. In a preferred embodiment, lead bricks, each having approximate dimensions of 2 by 4 by 8 inches, surround each testing station. Further, in order to prevent background radiation from entering the testing station through the opening through which the plunger 42a, 42b, ... 42n must enter the inner chamber of the testing station, each plunger includes a lead plug on each side of the test cell that seals the opening of the testing station whenever the plunger (and hence the holding receptacle and gemstone) is inserted fully therein. This sealing of the testing station is best illustrated relative to testing station 40b in FIG. 1. Testing station 40b has its plunger 42b fully inserted thereinto. In this position, the lead plugs together with the lead bricks form a solid lead shield around the test cell so as to completely seal the opening through which the plunger 42b enters the testing station.

The linear movement of the probe arms 46a, 46b, ... 46n is controlled in two stages by a main cylinder 48a, 48b, ... 48n, and a first auxiliary cylinder 54a, 4b, ... 54n. In the preferred embodiment, these are pneumatic cylinders; but any type of cylinder, e.g., hydraulic or electrical, could be used; as could any type of device that imparts linear (longitudinal) motion to the probe arms. The main cylinder 48a, 48b, ... 48n controls the movement of a carrier bracket 56a, 56b, ... 56n to which the first auxiliary cylinder is mounted. Movement of the plunger from its first position (also referred to as the "ready" position), where it is ready to receive a gemstone from the input conveyor 30, to its measurement position (also referred to as the "testing" position) inside of the testing station, and back again, is controlled exclusively by the main cylinder 48a, 48b, ... 48n. Movement of the plunger to its fully retracted position (also referred to as the "reject" position), where the holding receptacle is above the reject conveyor 60, requires that both the main cylinder and the first auxiliary cylinder be fully retracted.

In addition to linear movement of the probe arms 46a, 46b, ... 46n, a second auxiliary cylinder 58a, 58b, ... 58n is coupled to its respective probe arm through an appropriate linear-to-angular transducer 64a, 64b, ... 64n. As shown in FIG. 1, the second auxiliary cylinder 58a, 58b, ... 58n is mounted transverse to the longitudinal axis of the probe arms. Activation of the second auxiliary cylinder 58a, 58b, ... 58n causes the respective plunger 42a, 42b, ... 42n to rotate 180°, thereby causing the holding receptacle to be turned upside down, thus dumping or unloading the gemstone held therein. This unloading or dumping process is described more fully below in conjunction with FIGS. 3A-3D.

Figure 2:
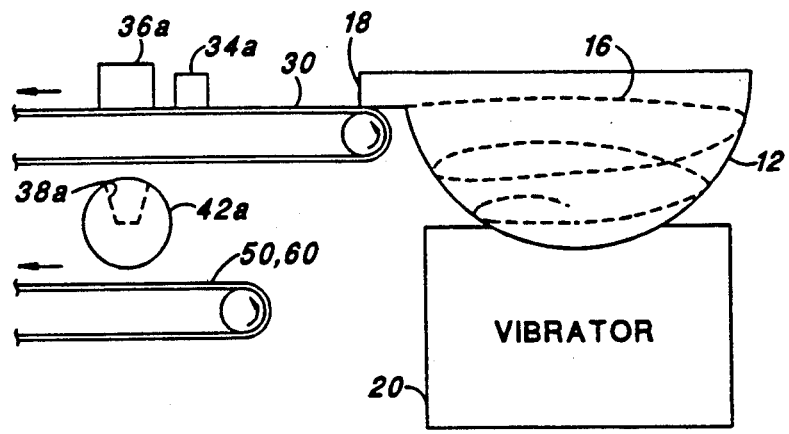
FIG. 2 is a schematic side view of the feeder portion of the gemstone sorting apparatus of FIG. 1.

FIG. 2 shows a schematic side view of the feeder portion of the gemstone sorting apparatus 10 of FIG. 1. As seen in FIG. 2, the feeder bowl 12 is supported by the vibrator 20. The exit port 18 of the feeder bowl, at the upper end of the spiral path 16 within the bowl, is positioned so as to direct the gemstones exiting therefrom onto the input conveyor 30. Also shown in FIG. 2 are the relative positions or locations of other selected elements of the sorting apparatus. Those shown in FIG. 2 include the optical sensor 34a, the puffer 36a, the accept and reject conveyors 50, 60, and the plunger 42a and its holding receptacle 38a.

Referring next to FIGS. 3A-3D, there is shown a sequence of schematic end views of the gemstone sorting apparatus of FIG. 1. The sequence of these figures clearly illustrates the manner in which the sorting apparatus 10 performs its function of moving a gemstone off of the input conveyor 30, into the testing chamber 40, and onto either the accept conveyor 50 or the reject conveyor 60. These figures further clarify the relative position and cooperation between the various elements of the sorting apparatus previously described in connection with the top schematic view of FIG. 1. It is noted that the reference numerals used in FIGS. 3A-3D are the same as those used in FIG. 1, but they do not use the letter designation used in FIG. 1 to depict different ones of the multiplicity of testing stations, holding receptacles, plungers, probe arms, cylinders, etc. Rather, the reference numeral 40, for example, as used in FIGS. 3A-3D, refers to one testing station, which may be any of the multiplicity of testing stations 40a, 40b, . . . 40n, that form part of the invention as shown in FIG. 1. Similarly, the reference numeral 46, as used in FIGS. 3A-3D, refers to one of the probe arms that may be any of the multiplicity of probe arms 46a, 46b, . . . 46n shown in FIG. 1.

Figure 3A:
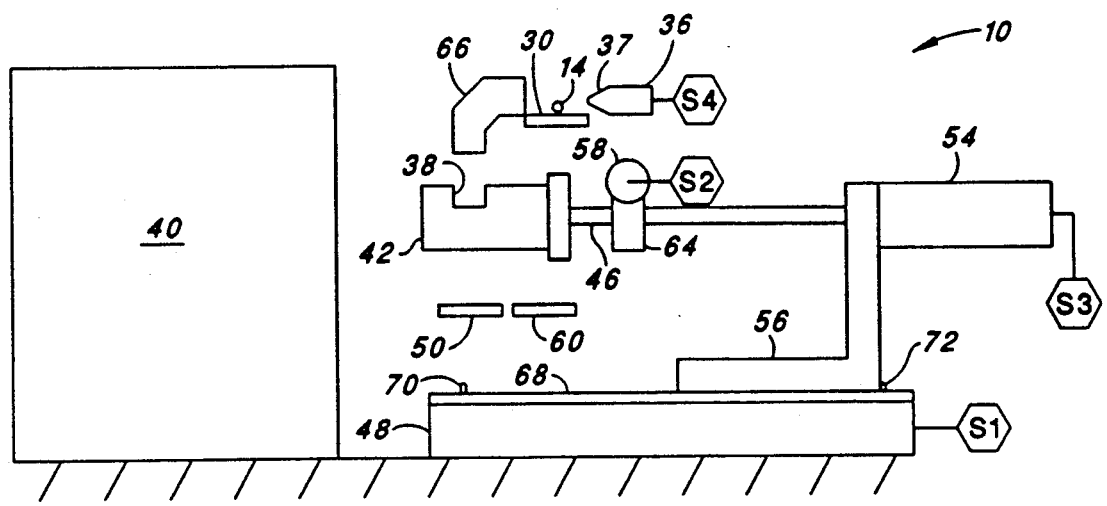
FIG. 3A is a schematic end view of the gemstone sorting apparatus of FIGS. 1-2 showing schematically an end view of the testing means, the delivery means, and the manipulating means of the invention prior to a gemstone being manipulated into a holding receptacle of a probe arm.

With reference to FIG. 3A, it is thus seen that the input conveyor 30 is positioned above the reject conveyor 60. The accept conveyor 50 is positioned at the same level as the reject conveyor and between the reject conveyor 60 and the testing station 40. The puffer 36 (which includes a nozzle 37) is positioned adjacent one side of the input conveyor 30. A solenoid valve S4 operates the puffer. When the solenoid valve S4 is activated, a puff of fluid, typically a suitable gas such as air, is directed out of the nozzle 37 in a narrow stream. This stream of air pushes the gemstone 14 off of the input conveyor 30 into a deflection chute 66, or equivalent, which deflection chute is opposite the puffer 36. The deflection chute 66 directs the gemstone 14 into the holding receptacle 38, or cup, of the plunger 42.

As shown in FIG. 3A, the plunger 42 and its respective holding receptacle 38 are positioned in a "ready" position of the sorting apparatus 10. In the "ready" position, the testing chamber 40 is vacant and ready to receive a gemstone. Moreover, the plunger 42 is positioned to receive a gemstone that is puffed off of the input conveyor 30.

The plunger 42 is placed in its "ready" position by moving the carrier bracket 56 all the way to one end of the main cylinder 48. Further, the first auxiliary cylinder 54 is controlled to hold the probe arm 46 in its maximum extended position; and the second auxiliary cylinder 58 is controlled to rotate the plunger so that the holding receptacle 38 is facing upwards, ready to receive and hold a gemstone 14. Note that a solenoid valve S1 controls the cylinder 48, another solenoid valve S2 controls the second auxiliary cylinder 58, and yet another solenoid valve S3 controls the first auxiliary cylinder 54. A suitable rail 68, or equivalent, allows the entire carrier bracket 56 to slide along its length between end switches or sensors 70 and 72, as controlled by the main cylinder 48. In the "ready" position shown in FIG. 3A, the carrier bracket 56 is moved all the way to the right (as oriented in FIG. 3A) against the end sensor 72.

Figure 3B:
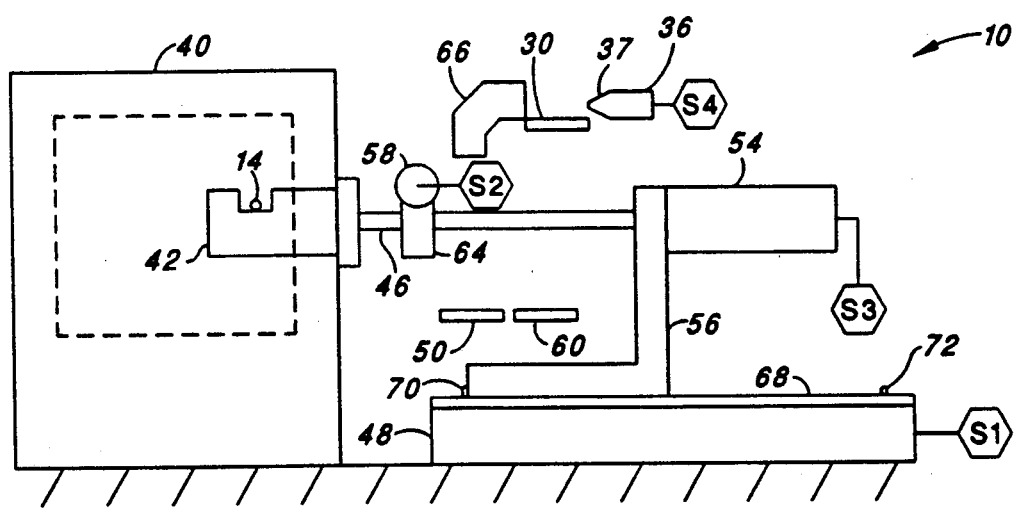
FIG. 3B is a schematic end view as in FIG. 3A showing the gemstone and holding receptacle in the testing position.

In FIG. 3B, a schematic end view of the sorting apparatus is shown similar to FIG. 3A, but with the apparatus being in a "testing" position. In the "testing" position, the main cylinder 48 is activated by solenoid S1 so as to move the carrier bracket all the way to the left end of the rail 68 (as oriented in FIG. 3B) against the end sensor 70. This motion causes the entire assembly supported by the carrier bracket 56 to also move to the left, causing the plunger 42 to be inserted into the testing chamber 40. The testing position is maintained sufficiently long for the radiation measurement of the gemstone 14 to be completed.

Figure 3C:
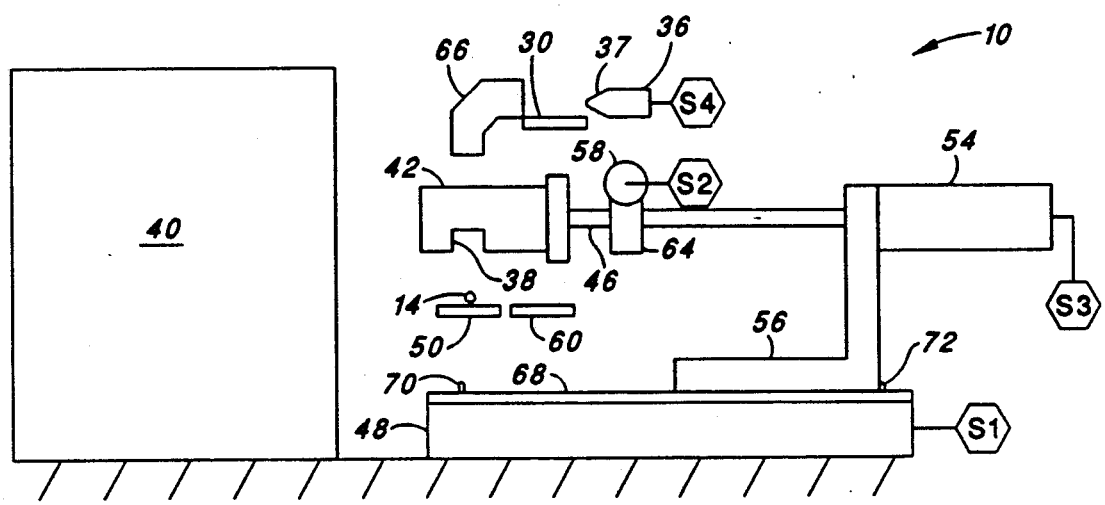
FIG. 3C is a schematic end view as in FIGS. 3A and 3B showing the gemstone and holding receptacle in the accept position.
Figure 3C:
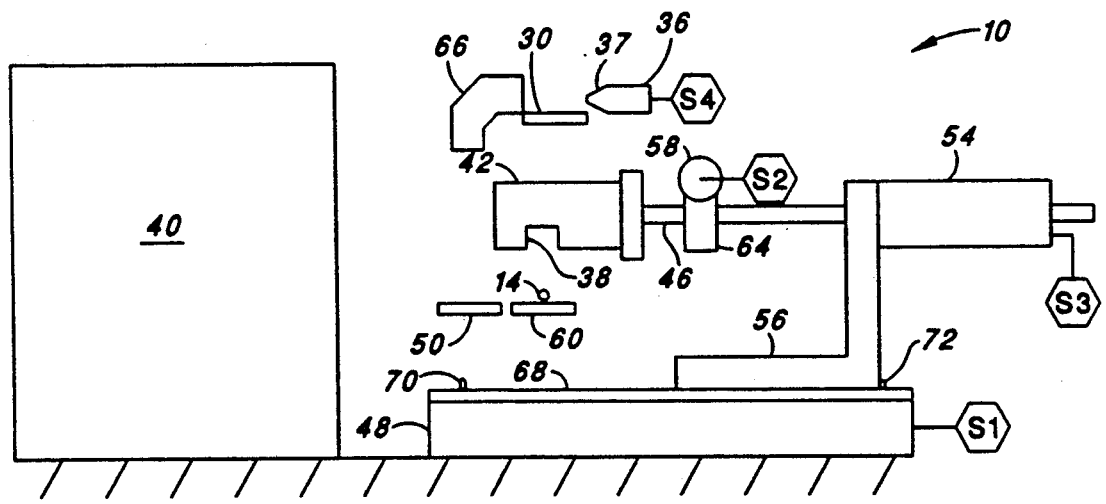

If the measurement of the residual radiation of the gemstone 14 indicates that the radiation level is less than the prescribed standard, then the gemstone is deemed "acceptable". As such, the sorting apparatus 10 is controlled to assume an "accept" position, as shown in FIG. 3C. This accept position is achieved in two steps. As a first step, the carrier bracket 56 is moved all the way to the right end (as oriented in FIG. 3C) of the rail 68 against the end sensor 72. This action retracts the plunger 42 from the testing station 40, and returns it to the "ready" position, as shown in FIG. 3A. As a second step, solenoid S2 is activated, causing cylinder 58 to rotate the probe arm 46 and plunger 42 180°. This causes the holding receptacle 38 to be tipped upside down. This action, in turn, allows the gemstone 14 held in the receptacle 38 to fall onto the accept conveyor 50.

If the measurement of the residual radiation of the gemstone 14 indicates that the radiation level is greater than the prescribed standard, then the gemstone is not acceptable. As such, the sorting apparatus is controlled to assume a "reject" position, as shown in FIG. 3D. This "reject" position is achieved in three steps. As a first step, the carrier bracket 56 is moved all the way to the right end (as oriented in FIG. 3D) of the rail 68 against the end sensor 72. This action retracts the plunger 42 from the testing station 40, and returns it to the "ready" position, as shown in FIG. 3A. As a second step, the first auxiliary cylinder 54 is activated by solenoid S3, causing the probe arm 46 to be further retracted, placing the plunger 42 and the holding receptacle 38 directly above the reject conveyor 60. As a third step, solenoid S2 is activated, causing the second auxiliary cylinder 58 to rotate the probe arm 46 and plunger 42 180°. This causes the holding receptacle 38 to be tipped upside down, allowing the gemstone 14 held in the receptacle 38 to fall onto the reject conveyor 60.

After unloading the gemstone onto the accept conveyor 50, as shown in FIG. 3C, or onto the reject conveyor 60, as shown in FIG. 3D, the sorting apparatus is controlled to return to the "ready" position, as shown in FIG. 3A. Once the "ready" position has been assumed, the apparatus is ready to receive another gemstone from the input conveyor 30 and repeat the cycle.

Figure 4:
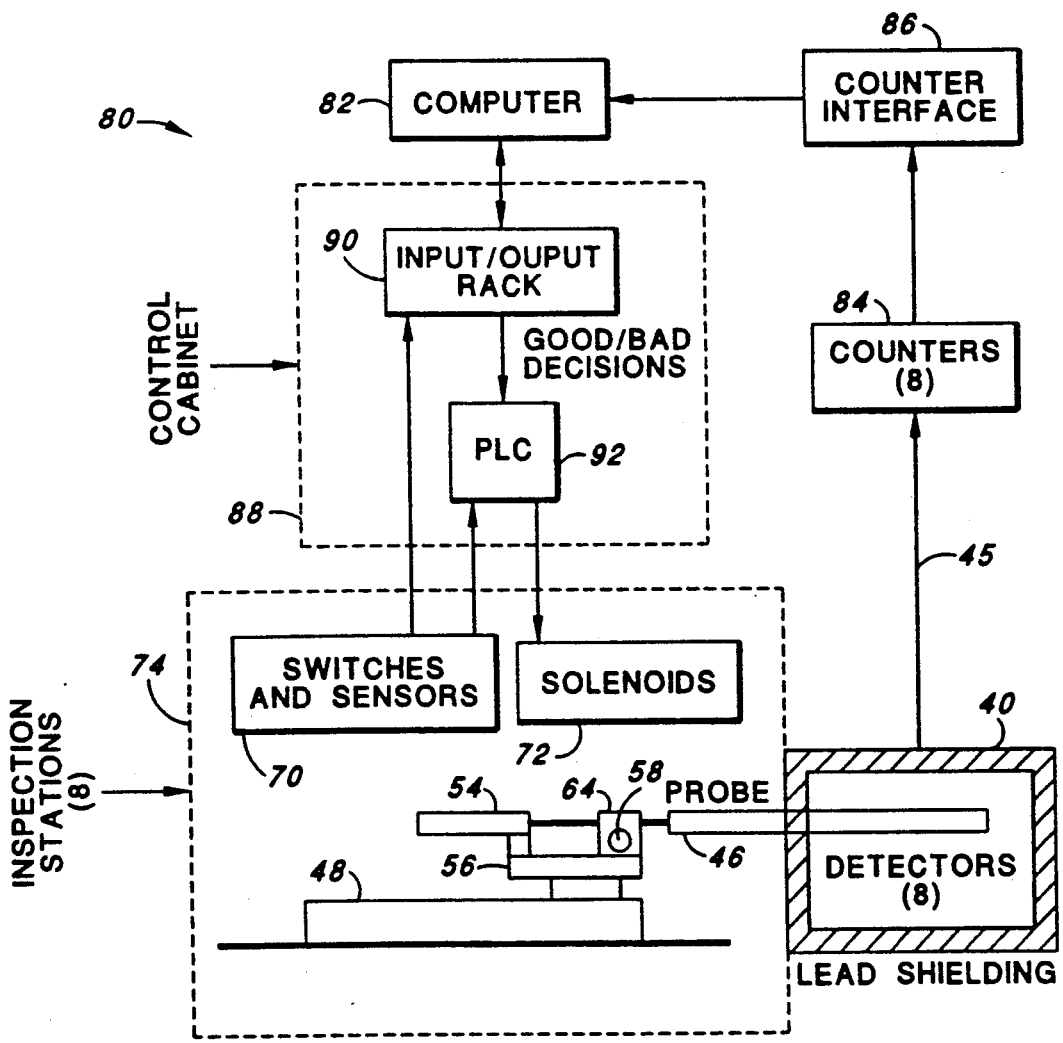
FIG. 4 is a block diagram of an automated gemstone sorting system, including the gemstone sorting apparatus of FIG. 1, made in accordance with the present invention.

FIG. 4 shows a block diagram of an automated gemstone sorting system 80 made in accordance with the present invention. The system includes a multiplicity of gemstone sorting stations 74 of the type shown and described in FIGS. 3A-3D. Each sorting station includes a corresponding testing station 40, as well as a probe arm 46 that selectively moves a gemstone into and out of the testing chamber 40. The inspection station 74 further includes a network of switches and sensors 70, as well as a network of solenoids 72 (e.g., the solenoids S1, S2, S3 and S4 shown in FIGS. 3A-3D), that are used to control the apparatus 10 as above described.

The overall sorting system 80 is controlled by a computer 82. The computer 82 monitors and logs the radiation measurements made at each of the testing stations and determines whether a given gemstone should be accepted or rejected. In a preferred embodiment of the system 80, eight separate inspection stations 74 are used, each having a testing chamber 40 associated therewith. However, it is to be understood that any reasonable number of inspection stations could be used.

The output of the crystal detectors in each testing station 40 is coupled to suitable radiation counting equipment 84 by way of a suitable cable 45. A separate counter is used for each testing station, with each counter providing a count signal indicative of the radiation associated with a particular gemstone held in the testing station. The output of the counters 84 is fed into the computer 82 by way of an appropriate counter interface circuit 86.

The computer analyzes the data received from the counters 84 in order to make an accept/reject decision. Once this decision is made, appropriate control signals are sent from the computer to a control cabinet 88. The control cabinet includes an input/output rack 90. This input/output rack 90 is essentially a junction box that interconnects and coordinates all of the controls and signals associated with the operation of the inspection stations 74 as controlled by the accept/reject decisions made by the computer 82. Many of these controls are pneumatic, as the cylinders used in the inspection stations are, in the preferred embodiment, pneumatic cylinders.

To facilitate control of the inspection stations 74, a programmable logic controller (PLC) 92 is also included within the control cabinet 88. This PLC allows the routine and repetitive logic decisions that must be made during the operation of a given inspection station 74 to be made independent of the computer 82. For example, a puffer 36 of a given inspection station cannot be activated unless the probe arm is in its "ready" position. Thus, a decision as to whether the puffer should be activated to move a gemstone off of the input conveyor 30 depends on the position of the probe arm at the time the gemstone is sensed. This decision, in turn, can be made by monitoring the status of the various sensors and switches 70 used in the inspection station, and need not require additional processing or input from the computer 82. Hence, the decision is made in the PLC 92 without tying up the processing capability of the computer. Once the cycle has begun, i.e., once a gemstone has been removed from the input conveyor, the PLC 92 maintains the operation of the inspection station, requiring only an accept/reject signal from the computer 82 at the conclusion of the radiation measurement. Once the accept/reject signal has been received, the PLC 92 again takes over control of the inspection station so as to direct the gemstone to either the accept or reject conveyor, return the probe arm to its rest position, and reload the probe arm with a new gemstone as soon as one is available.

Any suitable programmable processor may be used as the PLC 92. In the preferred embodiment, an Omron Sysmac C200H Programmable Logic Controller, coupled to an Omron Sysmac C200HME831 16k memory expansion, is used as the PLC.

Figure 5A:
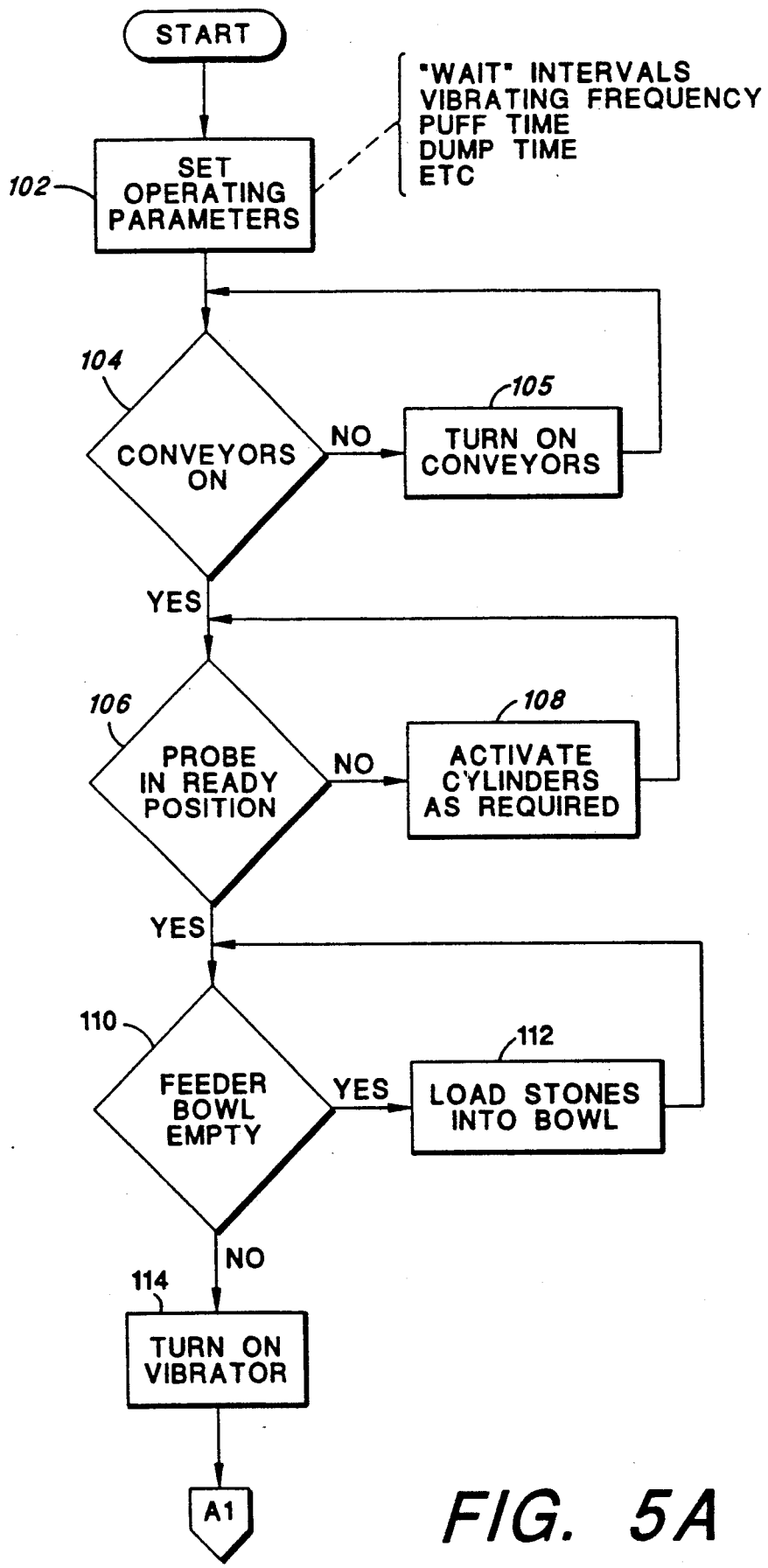
FIGS. 5A and 5B comprise a flow chart depicting the method and sequence used by operating personnel and/or the programmable logic controller (PLC) of FIG. 4 to control the movement of the gemstones through the sorting apparatus.
Figure 5B:
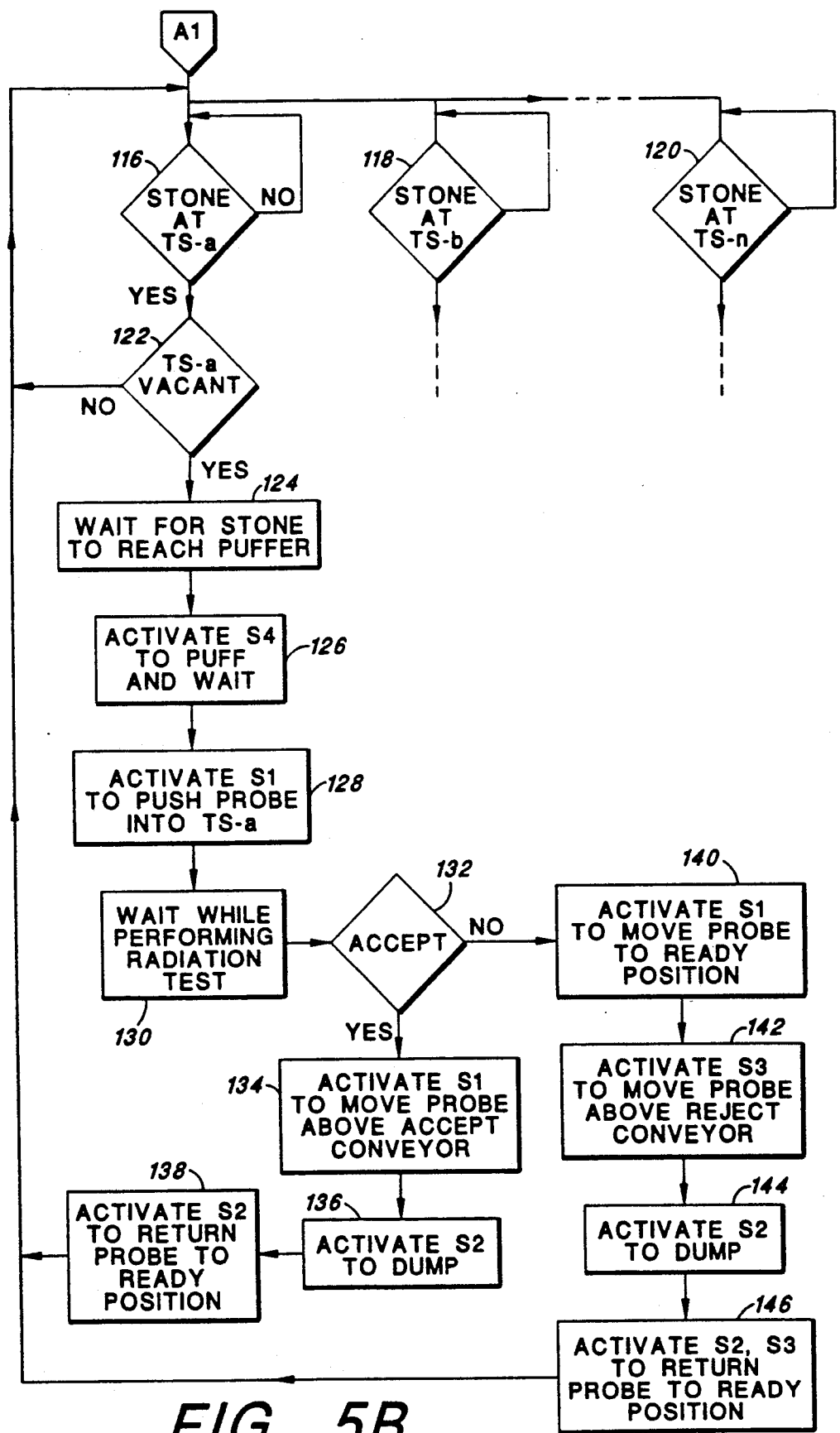

FIGS. 5A and 5B show a flow chart (which begins in FIG. 5A and continues in FIG. 5B) depicting the method and sequence used by operating personnel, the computer 82, and/or the programmable logic controller (PLC) 92 in order to efficiently operate the gemstone sorting system 80. In this flow chart, each major step or function is represented as a "block", with each "block" being referred to by a corresponding reference numeral. Those skilled in the art may readily program a suitable PLC, or equivalent, in order to carry out this method.

As seen in FIG. 5A, an initial step of the operating method involves setting the operating parameters (block 102) for the inspection station(s). These parameters include, for example, the "wait" intervals, or delays, that must elapse between certain prescribed events. For example, there is a wait interval or delay between sensing a gemstone on the input conveyor and activating the associated puffer in order to blow the gemstone into the receptacle of the probe arm. Similarly, there is a wait interval or delay after activating the unloading cylinder, in order to allow sufficient time for the gemstone to fall clear of the plunger at the end of the probe arm. Other parameters include the vibrating frequency, the puff time, the dump time, etc.

Once the operating parameters are set, a determination is made as to whether the conveyors are turned on (block 104). If not, they are turned on and set to an appropriate speed (block 105). Next, a decision is made as to whether the probe arm(s) is in the "ready" position (block 106). If not, the appropriate cylinders are activated in order to return the probe arms to the "ready" position (block 108). Then, a decision is made as to whether a batch of gemstones has been loaded into the feeder bowl (block 110). If not, then the gemstones are placed in the feeder bowl (block 112).

With the feeder bowl loaded, and with the probe arms of each inspection station in their "ready" position, and with the conveyors all turned on, the vibrator is next turned on (block 114) in order to walk the gemstones onto the input conveyor in single file. At this point, a decision is made as to whether a gemstone has arrived at the first test station, TS-a (block 116, FIG. 5B). This decision is made by monitoring the output of the optical sensor 34a associated with the first test station. Simultaneous with this determination, the output of the optical sensors associated with the other test stations, TS-b, . . . TS-n, is also monitored (blocks 118, 120). Operation of the other test stations occurs in parallel with, and independent of, the operation of the first test station. The operation of the other test stations follows the same sequence as for the first test station. Hence, only the flow chart for the first test station, TS-a, is shown in FIG. 5B once a gemstone has been sensed at the test station.

If a gemstone is sensed at TS-a (block 116), a decision is immediately made as to whether TS-a is vacant (block 122). In other words, a determination is made as to whether the probe arm of the test station is in its "ready" position. If not, no further action is taken at the test station, and the gemstone continues down the input conveyor to the next test station. If the test station is vacant, then there is a short delay (block 124) to allow the gemstone to reach the puffer. After this short delay, the puffer is activated in order to generate a short puff of air and another short delay begins (block 126). The short delay after the puff of air is to allow sufficient time for the gemstone to fall down the deflector chute into the holding receptacle of the probe arm. After such delay, the first solenoid S1 is activated in order to push the probe arm into the test station. Once within the test station, another delay is initiated (block 130). This delay allows the radiation measurement to be made.

After the measurement has been made, the computer 82 will issue an accept or reject signal (block 132). If an accept signal is issued, the solenoid S1 is appropriately activated (or deactivated) in order to move the probe arm above the accept conveyor (block 134). As shown in FIGS. 3A-3D, this position is the same as the "ready" position, thereby simplifying the controls needed to operate the inspection station. Once in this position, solenoid S2 is activated in order to dump the gemstone onto the accept conveyor (block 136). Thereafter, solenoid S2 is again activated (or deactivated) in order to return the probe to its "ready" position, with the holding receptacle upright ready to receive the next gemstone.

If a reject signal is issued (block 132), solenoid S1 is appropriately activated in order to move the probe arm back to its ready position (block 140). Then, solenoid S3 is activated in order to move the probe arm above the reject conveyor (block 142). Next, solenoid S2 is activated in order to dump the gemstone onto the reject conveyor (block 144). Thereafter, solenoids S2 and S3 are appropriately activated (deactivated) in order to return the probe to its ready position (block 146).

Figure 6:
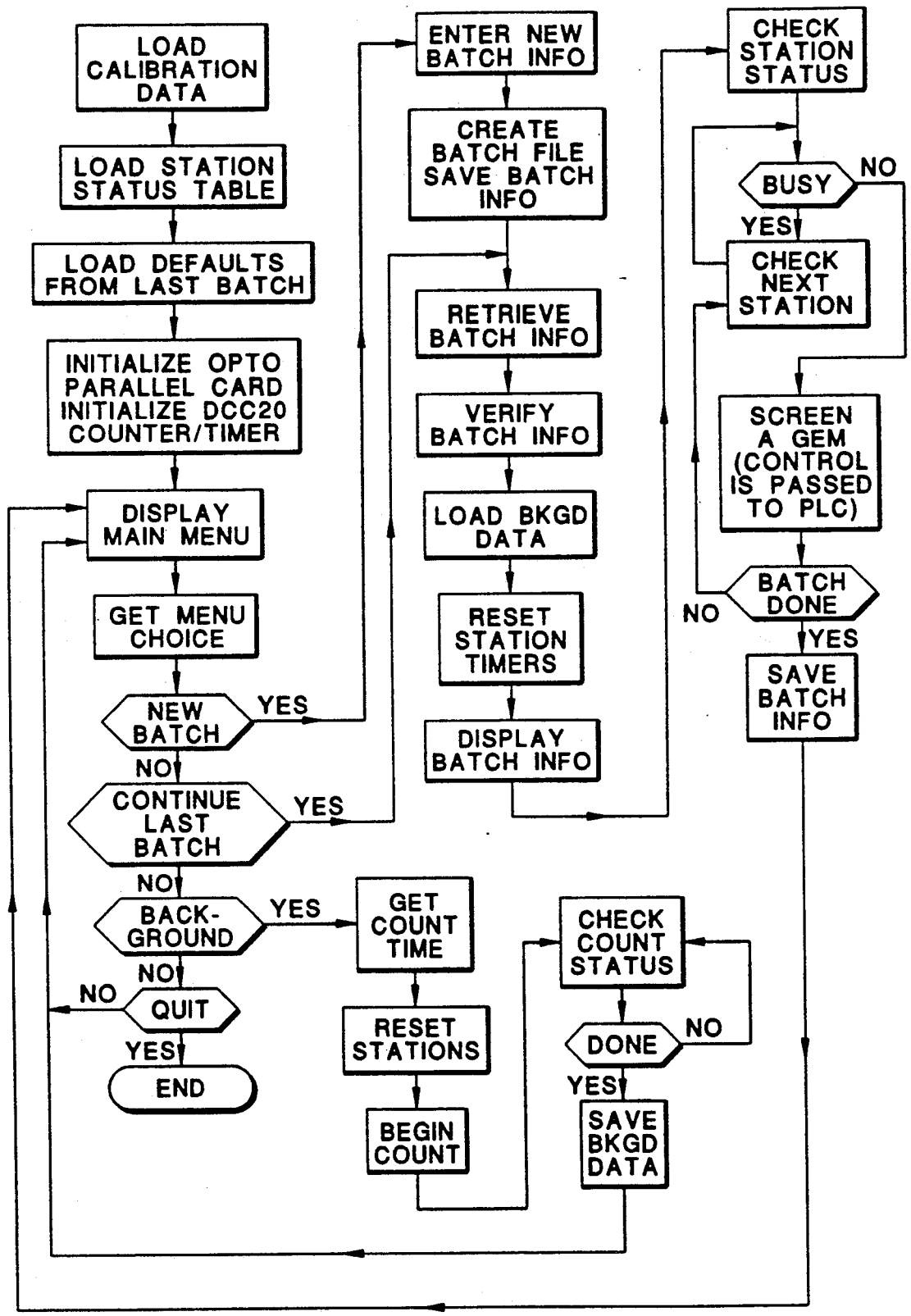
FIG. 6 is a flow chart of the control program for the computer of FIG. 4, illustrating the method employed by the computer to control the gemstone sorting system of FIG. 4.

FIG. 6 is a flow chart of the control program for the computer 82 of FIG. 4, illustrating the method employed by the computer to control the gemstone sorting system 80. This flow chart is self explanatory to those skilled in the art. It shows how the computer makes the accept/reject decision, and how the various measurement data is processed and logged in order to provide reports concerning the operation of the system.

Advantageously, the computer 82 tracks all of the data associated with sorting a given batch of gemstones, and is capable of calculating and reporting batch statistics, e.g., the number of gemstones accepted or rejected at a particular inspection station, the total accept/reject numbers for all stations, the accept/reject ratio, etc.

The computer 82 may be realized using any suitable AT 286/386/486 computer, or equivalent. In the preferred embodiment, the computer 82 is realized with a Datel 80286 computer, having 640K of RAM, a Seagate 40Mb hard disk drive, a Siiig model A.3 RS232 serial port, an Opto 22 model AC5 parallel port an Industrial Computer Source model DCC20 counter/timer card, and a Global model 425 backup power system. The serial port is used to output the accept/reject signals to the input/output rack 90 of the control cabinet 88, as well as to receive any important status signals from the switches and sensors 70 of the inspection station 74. The parallel port is used to receive the radiation measurement data from the counters 84. These serial/parallel port assignments could, of course, be reversed under appropriate conditions, if desired.

The counters 84 (FIG. 4) may be realized using any suitable commercially available ratemeter, such as the Ludlum model 2200 scaler ratemeter. A separate ratemeter is used for each test station. Such ratemeters are modified to provide 0–5 volt pulse output from the front panel. Such ratemeter functions not only as a counter, but also provides the high power needed by the NaI crystal detectors in each test station.

The switches, sensors, and other controls used in the inspection stations may be obtained from any suitable commercial source. In the preferred embodiment of the invention, the conveyors are realized using a variable speed electric motor obtained from Graham Company, model 302CM1-1; and a Dorner #SFA6-6/3.3 electric motor. These motors each drive a Boston Gear #F713-10-B5-0 90° speed reducing gearbox. Also used are three Dorner 4100 series 1½" conveyors.

The vibrator 20 and related parts are realized in the preferred embodiment using an FMC Syntron model CTRC1A electric controller and an FMC Syntron model 5EB051 magnetic parts feeder.

The probe arm and related components are realized in the preferred embodiment using a Bimba #PT-017-180 rotary actuator; five Bimba #MRS-087-BL magnetic reed switches; and a Bimba linear actuator. Also utilized as part of each inspection station are a Tol-o-matic #MPLSMN linear actuator, four MAC model 45A-SA2-DDAA-1BA solenoids, a MAC air manifold, and an Omron model E3XR-CE4 fiber optic photoswitch.

As described above, it is thus seen that the present invention provides a gemstone sorting apparatus that automatically sorts and classifies irradiated gemstones according to the residual radiation level of each gemstone. Advantageously, such sorting apparatus allows the sorting and classifying function for a given gemstone to be carried out simultaneous to the sorting and classifying function associated with a multiplicity of other gemstones. Hence, the throughput rate of the apparatus is not limited by the handling and processing time associated with a single gemstone or small parcel of gemstones.

Further, as is also evident from the above description, the present invention provides a gemstone sorting apparatus that allows the gemstones being classified to be loaded into a single input receptacle, and that thereafter automatically delivers the gemstones having an acceptable residual radiation level to a first output receptacle, and delivers the gemstones having an unacceptable residual radiation level to a second output receptacle.

Moreover, it is seen from the above description that the present invention includes an automated gemstone classifying system that automatically keeps track of the number of gemstones that are examined in a given batch of gemstones, including providing a visual and/or written report of such number. Such classifying system advantageously includes processing means that selectively computes the accept/reject statistics of a given batch of gemstones, or similar processing data, and provides a visual and/or written report of the same.

In addition, it is seen that the present invention provides a method of automatically classifying a group of gemstones, e.g., topaz, that has been previously irradiated according to the amount of residual radiation emanating from each gemstone within the group.

While the invention herein disclosed has been described by means of specific embodiments and applications thereof, numerous modifications and variations could be made thereto by those skilled in the art without departing from the scope of the invention set forth in the claims.

What is claimed is:

1. Apparatus for automatically sorting previously irradiated gemstones, comprising:
 (1) transport means for moving the gemstones from an initial location to classified final locations, said transport means including an input conveyor, an accept conveyor, and a reject conveyor;
 (2) testing means for determining if the residual gamma radiation of the previously irradiated gemstones is within prescribed limits, said testing means including a multiplicity of isolated testing chambers located to the side of the input conveyor, each of said multiplicity of isolated testing chambers having radiation measurement apparatus associated therewith for generating test data, said test data providing an indication as to whether the residual gamma radiation of a particular gemstone placed within a given one of said isolated testing chambers is within prescribed limits;
 (3) loading means for automatically loading the gemstones in an orderly fashion onto the input conveyor; and
 (4) moving means for moving the gemstones off of the input conveyor into the testing means and for moving the gemstones out of the testing means onto one of either the accept conveyor or the reject conveyor as a function of the whether the residual gamma radiation of the gemstones is within the prescribed limits as determined by the testing means, said moving means including:

a multiplicity of individual robot stations located on the side of the input conveyor opposite said multiplicity of isolated testing chambers, a respective robot station being associated with each isolated testing chamber, each robot station having a probe arm with a receptacle at one end for holding a gemstone; said probe arm being responsive to control signals so as to selectively: (1) move said receptacle (a) into or out of the respective isolated testing chamber, (b) above said accept conveyor, or (c) above said reject conveyor, and (2) rotate said receptacle in order to dump a gemstone held therein to a location below said receptacle;

a multiplicity of sensors, each of said sensors being associated with a respective one of said robot stations and isolated testing chambers, each of said sensors including means for sensing the presence of a gemstone on said input conveyor adjacent its associated robot station;

transfer means responsive to said control signals for transferring a gemstone from said input conveyor into the first vacant receptacle of one of said probe arms, whereby gemstones are transferred from said input conveyor into the first available receptacle of a probe arm; and control means responsive to preprogrammed data, test data from said testing means, and said sensors for generating said control signals so as to move a gemstone into a vacant test chamber, and thereafter transfer the gemstone from the test chamber to either the accept conveyor or the reject conveyor as a function of the test data.

2. The gemstone sorting apparatus as set forth in claim 1 wherein said transfer means comprises a fluid nozzle responsive to the sensing of gemstones by said sensing means for directing a puff of fluid at a specified point on the input conveyor when a gemstone is sensed at the specified point and when there is a vacant receptacle of a probe arm adjacent said specified point, whereby said gemstone is transferred from said input conveyor to said vacant receptacle by said puff of fluid.

3. The gemstone sorting apparatus as set forth in claim 2 wherein the fluid directed by said fluid nozzle at the gemstone on said input conveyor comprises air.

4. The gemstone sorting apparatus as set forth in claim 3 further including processing means for tracking and logging the gemstones that pass through said sorting apparatus, and for generating reports indicating how many gemstones in a given batch of gemstones have been sorted into an accept or reject category.

5. An automated classifying system for classifying irradiated gemstones according to residual radiation levels, said classifying system comprising:

(a) first transport means for automatically moving each gemstone in a batch of gemstones from an initial location to one of a multiplicity of testing stations, said first transport means including:

(1) a feeder bowl into which said batch of gemstones is placed, said feeder bowl having a spiralling path around its inside edge that spirals from the bottom of the bowl to an upper edge;

(2) vibrating means for vibrating said feeder bowl at a controlled frequency, the gemstones in said feeder bowl being caused to move up said spiralling path by the vibrations caused by said vibrating means;

(3) an input conveyor positioned to receive gemstones that have moved up said spiraling path and that fall out of said feeder bowl, the rate at which said gemstones fall out of said feeder bowl being controlled by controlling the frequency of said vibrating means, said input conveyor being further positioned to carry the gemstones that fall thereon past each of said multiplicity of testing stations; and (4) removal means for removing a gemstone from said input conveyor adjacent a vacant testing station, said removal means includes a pneumatic puffer that selectively directs a puff of air at a specified location on the input conveyor where a gemstone is sensed to be, said puff of air directing said gemstone off of said input conveyor towards one of said multiplicity of testing stations.;

(b) measurement means for automatically measuring the radiation of each gemstone moved to one of said multiplicity of testing stations;

(c) second transport means for automatically removing a gemstone from a given testing station after its radiation has been measured and moving it to one of a plurality of final locations as a function of the radiation measured by the measurement means, said second transport means including:

(1) a movable receptacle into which a gemstone removed from said input conveyor is placed;

(2) actuator means for selectively moving said receptacle to position it inside of said measurement means or above one of a plurality of deposit locations; and (3) means for unloading a gemstone held in said receptacle to a selected one of said deposit locations; and (d) processing means for monitoring and controlling said first and second transport means and measurement means so as to move a new gemstone into a given testing station immediately after said second transport means has removed a gemstone therefrom;

whereby all of the gemstones in said batch of gemstones are transported through and classified by said classifying system in an efficient manner.

6. The automated classifying system as set forth in claim 5 wherein said movable receptacle is placed at one end of a probe arm, said probe arm being longitudinally controlled by said actuator means.

7. A method of automatically sorting a batch of gemstones in accordance with the residual gamma radiation level of each gemstone within said batch of gemstones comprising the steps of:

(a) moving each gemstone in the batch of gemstones from an initial location to one of a multiplicity of testing stations by:

(1) loading the batch of gemstones into a feeder bowl, said feeder bowl having a spiralling path around an inside edge thereof;

(2) vibrating the feeder bowl at a preselected frequency, which vibrating causes the gemstones in said batch of gemstones to work their way up said spiralling path and exit said feeder bowl one at a time;

(3) loading the gemstones exiting said feeder bowl onto an input conveyor that carries the gemstones past said multiplicity of testing stations in series; and (4) removing a given gemstone from the input conveyor at the first vacant testing station of said multiplicity of testing stations that said given gemstone passes, and inserting said gemstone into said vacant testing station by sensing when the given gemstone is adjacent a vacant testing station, blowing the given gemstone off of the input conveyor with a controlled puff of gas into a holding receptacle at the end of a probe arm, and longitudinally moving the probe arm so as to insert the gemstone inside of the vacant testing station;

(b) measuring the residual gamma radiation of each gemstone moved to one of said multiplicity of testing stations by:
  (1) inserting each gemstone into a shielded chamber that prevents radioactive gamma particles from passing therethrough,
  (2) closing said chamber, and
  (3) detecting and counting the radioactive gamma particles emitted from said gemstone within a prescribed period of time,
  (4) whereby radioactive gamma particles associated with background radiation are not included in the radiation measurement thus made;

(c) removing a gemstone from a given testing station after its residual radiation has been measured and moving it to one of a plurality of final locations as a function of the radiation measured for such gemstone at that given testing station;

(d) automatically monitoring and controlling the movement, testing and removing of the gemstones performed in steps (a), (b) and (c) so as to move a new gemstone into a given testing station immediately after a previous gemstone has been removed therefrom, whereby all of the testing stations are continually being loaded with a gemstone, testing a gemstone, or having a gemstone removed therefrom, whereby the batch of gemstones are automatically sorted in as short of time as possible.

8. The method of automatically sorting a batch of gemstones as set forth in claim 7 wherein step (c) of removing a gemstone from a given testing station after its residual radiation has been measured and moving it to one of a plurality of final locations includes:

longitudinally moving said probe arm out of said testing chamber a prescribed distance, said prescribed distance being one of a plurality of possible extraction distances, said prescribed distance being selected as defined by the amount of residual radiation measured for the gemstone while inside of the testing chamber;

unloading said gemstone out of said holding receptacle onto one of a plurality of output conveyors, a respective output conveyor being positioned to receive said gemstone at each of said plurality of possible extraction distances; and carrying the gemstones on said plurality of output conveyors to corresponding collection bins;

whereby the gemstones are sorted into said collection bins as a function of the residual radiation measured for each gemstone.

* * * * *